United States Patent [19]
Wong et al.

[11] Patent Number: 5,876,701
[45] Date of Patent: Mar. 2, 1999

[54] STRIPED TOOTHPASTE STABLE TO COLOR BLEEDING

[75] Inventors: Mike Wong, North Brunswick; Michael Prencipe, West Windsor, both of N.J.

[73] Assignee: Colgate Palmolive Company, New York, N.Y.

[21] Appl. No.: 32,576

[22] Filed: Feb. 27, 1998

[51] Int. Cl.$^6$ ..................................................... A61K 7/16
[52] U.S. Cl. ................ 424/49; 424/7.1; 424/10; 424/50; 424/51; 424/52; 424/53; 424/54; 424/55; 424/56; 424/57; 424/58; 424/484; 424/486; 426/223; 426/262; 426/321; 426/533; 426/534
[58] Field of Search .................. 424/71, 10, 49, 424/50, 51, 52, 53, 54, 55, 56, 57, 58, 484, 486; 426/321, 262, 223, 533, 534

[56] References Cited

U.S. PATENT DOCUMENTS

| | | | |
|---|---|---|---|
| 3,929,988 | 12/1975 | Barth | 424/54 |
| 3,957,964 | 5/1976 | Grimm, III | 424/49 |
| 3,980,767 | 9/1976 | Chown et al. | 424/52 |
| 4,071,614 | 1/1978 | Grimm, III | 424/49 |
| 4,144,323 | 3/1979 | Lamberti | 424/54 |
| 4,202,878 | 5/1980 | Ritze | 424/49 |
| 4,348,378 | 9/1982 | Kosti | 424/7 |
| 4,358,437 | 11/1982 | Duke | 424/52 |
| 4,568,534 | 2/1986 | Stier et al. | 424/7.1 |

*Primary Examiner*—James O. Wilson
*Attorney, Agent, or Firm*—Paul Shapiro

[57] ABSTRACT

A striped and/or speckled dentifrice stable to color bleeding, wherein at least one dentifrice component contains a colorant entrained in a high density polyethylene matrix having a melting point range as measured by DSC is between about 110° C. and about 145° C., whereby on storage substantially no visually observable colorant bleeding is present in any other dentifrice component.

9 Claims, No Drawings

STRIPED TOOTHPASTE STABLE TO COLOR BLEEDING

BACKGROUND OF THE INVENTION

1. Field of the Invention

This invention relates to an aesthetically pleasing pleasant tasting multicomponent dentifrice and more particularly to a striped toothpaste or gel wherein there is substantially no colorant bleeding between dentifrice components.

2. The Prior Art

Aesthetic effects have been acknowledged to play an important role in consumer acceptance of many products. In many cases, ornamental effects have been used to distinguish particular products in the marketplace and to identify products having particular distinctive properties. In the dentifrice field, toothpastes and gels which have incorporated therein contrasting colored stripes or speckles are known. Such stripes or speckles provide an aesthetic effect which the user finds pleasing and promotes the use of the dentifrice.

A major problem impacting the aesthetic appearance of striped toothpaste is the bleeding or migration of color from one component into another. This is especially severe if one colored component is applied to the surface of a white base. For this reason, a colorant that exhibits substantially no visible bleeding is required.

Striped dentifrice products containing water-soluble dyes are known in the prior art as for example, as disclosed in U.S. Pat. Nos. 4,358,437, 4,568,534, and 4,487,757. A disadvantage to the use of water-soluble dyes enumerated in these patents is that visible bleeding is observed.

U.S. Pat. Nos. 3,957,964, 3,929,988, 4,071,614 and 4,348,378 disclose dentifrices containing encapsulated ingredients such as flavors whereby such ingredients are maintained substantially separate from other dentifrice ingredients during manufacture and storage, while subsequently releasing the encapsulated ingredients into the dentifrice during tooth brushing.

It is also known to the art, e.g., U.S. Pat. No. 4,202,878 to encapsulate water insoluble dyes in capsules wherein the shell material is formed from non-toxic naturally occurring waxes such as carnauba wax, candelella wax, castor wax, paraffin wax and bayberry wax. Although encapsulation of the dyes in these waxes overcome dye migration to some extent, undesirable levels of bleeding persist during accelerated aging conditions, as for example storage of the striped dentifrice for 4–6 weeks at 50° C.

Accordingly, there is a need for a colorant composition useful in the striping of dentifrices which will essentially eliminate visible colorant bleeding.

SUMMARY OF THE INVENTION

By analyzing data on the temperature increase observed by subjecting a thermoplastic material to differential scanning calorimetry using a differential scanning calorimeter (DSC), it is possible to observe a state change of the material under heat application and heat absorption peaks accompanying phase transition and melting of the thermoplastic material.

In accordance with the present invention, there is provided an aesthetically pleasing, pleasant tasting, substantially non-bleeding, striped dentifrice composition comprised of at least two dentifrice components wherein at least one of the components is a paste or gel containing a colorant entrained in a matrix of a high density polyethylene having a melting point range, as determined by DSC, between about 110° and about 140° C.

As will hereinafter be demonstrated, the high density polyethylene entrained colorants of the present invention unexpectedly are substantially non-bleeding when present in conventional toothpaste or gel formations, particularly when contrasted with similar colorants entrained in wax and synthetic polymeric resins including paraffin wax and low density polyethylene. It is believed that the molecular weight, degree of crystallinity, and degree of branching groups of high density polyethylene as reflected by its melting point is responsible for the superior non-bleeding properties of colorants entrained in this polymer. For example, HDPE is more crystalline in nature and has a lesser degree of branching than LDPE and paraffin waxes and is significantly superior to these latter materials in the preparation of non-bleeding colorants for striped toothpaste products.

DESCRIPTION OF THE PREFERRED EMBODIMENTS

The term "high density polyethylene" (HDPE) as used in the specification and claims includes within its meaning homopolymers and copolymers of ethylene which exhibit a density of 0.94 to 0.97 g/cc, preferably 0.947 to 0.965 g/cc. These polymers may be ethylene homopolymers or ethylene copolymers of alphaolefins containing a minor amount, preferably about 0.1 to 25 mole percent of an olefin, preferably a 1-olefin, containing 3 to 10 carbon atoms, e.g., 1-propene, 1-butene, 1-pentene, 1-hexene, 4,methyl-1-pentene, 1-heptene, and 1-octene. The preferred olefin cornonomers are 1-butene, 1-hexene and 1-octene.

The flow index or high load melt index of the HDPE (measured at 190° C. in accordance with ASTM D-1238, Condition F) is generally at least about 5.0, preferably from about 6.0 to 8.0 and most preferably about 6.5 to 8.0 g/10 min.

The HDPE entrained colorant particles are incorporated in the dentifrice component at a concentration of about 0.01 to about 5% by weight and preferably about 0.05 to about 1% by weight.

Colorants suitable for entrainment or encapsulation in the HDPE matrix in accordance with the practice of the present invention include physiologically compatible water-soluble dyes and lakes including natural or synthetic dyes of the types permitted in foods and drugs, such as those listed in Title 21 of the U.S. Code of Federal Regulations, Section 74, including for example FD&C Blue #1 and FD&C Yellow #10. In addition to these water-soluble dyes, it is also possible to use water-insoluble dyes, for example Eyeshadow Blue KO, Colour Index 77 510, EG-No., Blue 15 (C-Blue 17), or mixtures of water-insoluble dyes and water-soluble dyes, for example Eyeshadow Blue KO and Lemon Yellow ZN 3, in which case green hues are obtained. Preferred colorants are comprised of 0.1% to 40% by weight, preferably 7% to 30% by weight, of a water soluble dye on a substrate such as alumina, zirconia and titania and preferably alumina hydrate. Preferred lakes are those certified by the Color Certification Laboratory of the Food and Drug, Administration of the Health, Education and Welfare Department of the United States Government, for example, F.D. & C. Blue No. 1 Lake, F.D. & C. Blue No. 2 Lake, F.D. & C. Red No. 3 Lake, F.D. & C. Yellow No. 5 Lake and F.D. & C. Yellow No. 6 Lake.

The colorant may be entrained in the HDPE matrix using methods of encapsulation which are known in the art. As these encapsulation methods are not specific parts of the present invention, they will not be described at length herein. Further disclosure of suitable encapsulation methods may be found in Kirk-Othmer Encyclopedia of Chemical Technology, Third Edition, Vol. 125 Pgs. 470–493 (1981).

An example of a method by which colorants such as lakes of the present invention may be entrained in a HDPE matrix, is by dispersing or dissolving the desired amount of colorant in HDPE that has been thermally softened to form a liquid composition. The desired amount of colorant material is that amount of colorant which results in a final concentration of up to 20% colorant, preferably 0.1–10% by weight colorant in the final colored HDPE particles cooled to room temperature. The liquid HDPE dispersion is agitated so that the liquid HDPE deposits on each entity of the dye or lake material forming liquid HDPE walled droplets. The dispersion is then cooled and milled to provide solid particles in which the dye or lake is entrained. The particle size distribution of the HDPE particles can vary from 10 to 1000 μm.

In the preparation of a dentifrice composition in accordance with the present invention, there is utilized an orally acceptable vehicle, including a water-phase with huinectant which is preferably glycerine or sorbitol or an alkylene glycol such as polyethylene glycol or propylene glycol, wherein the water is present typically in amount of about 5 to about 20% by weight and the glycerine, sorbitol and/or the alkylene glycol humectant ingredients typically total about 20–60% by weight of the dentifrice, more typically about 25 to 50%.

Abrasive compounds may be present in the dentifrice and include silica, insoluble sodium inetaphosphate, tricalcium phosphate, dihydrated dicalcium phosphate, calcium carbonate, aluminum silicate, hydrated alumina, sodium bicarbonate, and calcined alumina. Preferred abrasives include silica, and dicalcium phosphate. Silica abrasives useful in the practice of the present invention are available under the trade designation Zeodent 115. The abrasive is generally present in the dentifrice composition of the present invention in weight concentrations of about 15 to about 60% by weight.

Suitable thickeners or gelling agents used to prepare the dentifrice of the present invention include thickening silicas sold under the trade designation Zeodent 165, natural or synthetic organic materials including Irish moss, iota-carrageenan, gum tragacanth, starch, polyvinylpyrrolidone, hydroxyethylpropyl cellulose, hydroxybutyl methyl cellulose, hydroxypropyl methyl cellulose, hydroxyethyl cellulose and sodium carboxymethyl cellulose. The thickener or gelling agent is present in the dentifrice composition in proportions of about 0.1 to about 10% by weight, preferably about 2 to about 8% by weight.

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid inonoglyceride inonosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate and higher fatty acid esters of 1,2-dihydroxy propane sulfonate. The surfactant is typically present in the dentifrice compositions of the present invention in an amount of about 0.3 to about 5% by weight, preferably about 0.5 to about 2% by weight.

Anticaries agents which provide a source of fluoride ions may be included in the dentifrice composition in amount sufficient to supply about 25 ppm to 5,000 ppm of fluoride ions, such as soluble alkali metal salts, for example, sodium fluoride, potassium fluoride, and sodium monofluorophosphate.

In addition to fluoride compounds, there may also be included in the dentifrice composition antitartar agents such as pyrophosphate salts including dialkali or tetraalkali metal pyrophosphate salts such as $Na_4P_2O_7$, $K_4P_2O_7$, $Na_4K_2P_2O_7$, $Na4H_2P_2O_7$ and $K_2H_2P_2O_7$ long chain polyphosphates such as sodium hexametaphosphate, sodium tripolyphosphate and cyclic phosphates such as sodium trimetaphosphate which are included in the dentifrice composition at a concentration of about 1to about 5% by weight.

Synthetic anionic polycarboxylates may also be used in the dentifrice compositions of the present invention. Such anionic polycarboxylates are generally employed in the form of their free acids or preferably partially or more preferably fully neutralized water soluble alkali metal, e.g., potassium and preferably sodium or ammonium salts. Preferred polycarboxylate compounds are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are commercially available, for example, under the trade designation, as Gantrez, e.g. AN 139 (M.W. 500,000), AN 119 (M.W. 250,000); and preferably S-97 Pharmaceutical Grade (M.W. 70,000).

The dentifrice composition of the present invention may also contain a flavoring agent. The flavoring agent is incorporated in the dentifrice composition at a concentration of about 0.1 to about 5% by weight and preferably about 0.5 o about 1.5% by weight. Flavoring agents which are used in the practice of the present invention include essential oils as well as various flavoring aldehydes, esters, alcohols, and similar materials. Examples of the essential oils include oils of spearmint, peppermint, wintergreen, sassafras clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

Various other materials may be incorporated in the dentifrice compositions of this invention, including antibacterial agents such as Triclosan, chlorhexidine, desensitizers such as potassium nitrate, and potassium citrate, whitening agents such as hydrogen peroxide, calcium peroxide and urea peroxide, preservatives, silicones, and chlorophyll compounds. These adjuvants, when present, are incorporated in the dentifrice composition in amounts which do not substantially adversely affect the properties and characteristics desired.

The preparation of dentifrices compositions is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices according to the present invention.

Dentifrice striping can be accomplished by either of the two techniques common in the art, namely surface striping and deep striping. Surface striping is created by a special nozzle through which the dentifrice is extruded from a tube or pump dispenser, wherein a separate reservoir of stripe material is positioned so that the initial deposition of the stripe on the base dentifrice segment is during extrusion. In deep striping systems by contrast, the layers of striping and base material are juxtapositioned in the dispenser in the pattern of the desired stripes, hence the initial deposition of the stripe on the base dentifrice is prior to extrusion from the dispenser. With surface striping, the quantity of striping material to base material in surface striping is generally in the ratio of about 5:95 to about 20:80; whereas, in deep striping the range can extend from about 10:90 to about 50:50. U.S. patents which further exemplify such striping methods include U.S. Pat. Nos. 3,969,767, 3,135,428, 2,914,220, 2,905,364, 2,873,887 and 2,789,731.

The following example is illustrative of the subject invention, and does not limit it. All parts or percentages are by weight and all temperatures are in degrees C., unless specifically stated to be otherwise.

EXAMPLE

A striped blue/white dentifrice formulation was prepared in which one dentifrice component (Dentifrice A) contained as the colorant a water soluble FD&C Blue #1 Lake (alumina) dye entrained in HDPE and the other TiO$_2$ (Dentifrice B). The FD&C Blue #1 dye was entrained in a HDPE matrix by heating the HDPE resin to above its melting point to liquefy and then dispersing the dye in the hot melt. As the dispersion was allowed to cool, large pieces of the HDPE reformed containing the dye which comprised about 3% by weight of the HDPE matrix. The cooled pieces were then ground to a particle size of about 30 to 120 μm.

The ingredients of Dentifrice A and B are listed in Table I below.

TABLE I

| | Dentifrice | |
|---|---|---|
| Ingredient | A | B |
| Glycerin 99.7% | 20.0 | 20.0 |
| Carrageenan | 0.3 | 0.3 |
| Carboxymethyl cellulose | 0.8 | 0.8 |
| Sodium saccharin | 0.3 | 0.3 |
| Sodium hydroxide | 1.20 | 1.20 |
| Water, deionized | 17.557 | 18.057 |
| Zeodent 115 | 20.0 | 20.0 |
| Zeodent 165 | 1.3 | 1.3 |
| Sodium fluoride | 0.243 | 0.243 |
| Sorbitol (70%) | 19.5 | 19.5 |
| TiO$_2$ | — | 0.5 |
| Flavor | 1.0 | 1.0 |
| Sodium lauryl sulfate | 1.5 | 1.5 |
| HDPE Entrained Lake* | 1.0 | — |
| Gantrez S-97 | 15.0 | 15.0 |
| Triclosan | 0.3 | 0.3 |
| TOTAL | 100.00 | 100.00 |

*HDPE CAS Registry Number 26221-73-8.

To determine bleeding levels, toothpaste tubes were filled with the blue colored Dentifrice A and white colored Dentifrice B using the deep striping filling system previously described whereby the striped portions were of equal volume. The tubes containing the striped dentifrice were aged at 50° C. for 4 and 6 week time periods. To determine the level of bleeding that occurred during aging, a striped sample of at least 4 inches in length was dispensed from the tubes onto a paper sheet. With the end of a capillary tube (90 mm diameter—closed end), a 0.1 gram toothpaste sample was taken about 0.1–0.2 inches from the blue-white stripe interface. The paste sample was dissolved in 1 milliliter (ml) water and stirred in a Vortex to ensure a complete mixture of the sample so that the dye in the paste was resolubilized in the water phase. The sample was then centrifuged for 2–3 minutes to separate the supernatant (containing the dissolved dye) from the other dentifrice ingredients. Using an ultraviolet visible spectrophotometer, the extinction coefficient at the wavelength at which maximum absorbance of light occurs (lambda max) that is, 630 nm for FD&C Blue 1 was determined before and after aging. The amount of dye that migrated from the blue striped gel to the white paste was determined from Beers Law:

$$A = \Sigma l c$$

where
A=absorbance at λmax
Σ=extinction coefficient for dye (cm$^{-1}$M$^{-1}$)
l=length of sample cell (usually 1 cm)
c=concentration (M)

The percent dye bleeding was calculated by dividing absorbance of the FD&C Blue-1 dye detected in the white paste component versus a control. The results are recorded in Table II below.

For purposes of comparison, the above identified procedure was repeated except the blue lake was separately entrained in several different thermoplastic matrices, namely a refined paraffin wax having a melting point of 25°–70° C. a synthetic paraffin wax having a melting point of 45° C.–80° C., and a low density (0.93 g/cc) polyethylene having a melting point of 125° C. These dentifrice compositions containing the comparative colorants were subjected to the same aging tests performed in Example. The bleeding results for these comparative colorants also recorded in Table II below.

TABLE II

| Encapsulant Matrix | Aging @50° C. Weeks | Absorbance @ 630 nm Paste Side | % Bleeding Detected in White Paste |
|---|---|---|---|
| HDPE | 4 | 0.2 | 0.6 |
| | 6 | 0.3 | 0.8 |
| Refined paraffin wax | 4 | 7.2 | 18.2 |
| | 6 | 9.0 | 22.6 |
| Synthetic paraffin wax | 4 | 7.0 | 17.5 |
| | 6 | 7.9 | 19.9 |
| LDPE | 4 | 5.0 | 12.5 |
| | 6 | 6.4 | 16.1 |
| No Colorant | 4 | 0.0 | 0.0 |
| | 6 | 0.0 | 0.0 |

The results recorded in Table II indicate that encapsulation of the blue lake in an HDPE matrix significantly reduced dye bleeding when present in a striped toothpaste product as compared to paraffin wax and LDPE matrices. The percent bleeding of 0.6–0.8% that occurred when the blue lake was encapsulated in HDPE matrix was not perceivable to the naked eye whereas bleeding at levels of 12.5–22.6% that occurred when the blue lake was encapsulated in the LDPE or refined and synthetic paraffin waxes was clearly visible to the naked eye.

We claim:

1. A multicolored dentifrice composition stable to color bleeding comprising a plurality of components, at least one component having a colorant entrained in a matrix of high density polyethylene (HDPE), the HDPE having a melting point range as determined by differential scanning calorimetry of between about 110° and about 140° C., whereby after storage, substantially no significant amount of colorant is observable as migrating into any other dentifrice component.

2. The composition of claim 1 wherein the HDPE has a density of 0.94–0.97 g/cc.

3. The dentifrice composition of claim 1, wherein the colorant is a physiologically compatible lake.

4. The composition of claim 1 wherein the multicolored composition is striped.

5. The composition of claim 1 wherein the multicolored composition is speckeled.

6. A method of preparing a non-bleeding striped dentifrice comprising preparing a plurality of different colored dentifrice components in physical interfacial contact and providing in at least one component a colorant entrained in a matrix of HDPE having a melting point range as determined by differential scanning calorimetry is between about 110° C. and about 145° C.

7. The method of claim 1 wherein the HDPE has a density of 0.94–0.97 g/cc.

8. The method of claim 4, wherein the colorant is a physiologically compatible lake.

9. The composition of claim 1 wherein the HDPE particles have a particle size of from about 30–about 1000 $\mu$m.

* * * * *